US011953490B2

(12) United States Patent
Zhu et al.

(10) Patent No.: US 11,953,490 B2
(45) Date of Patent: Apr. 9, 2024

(54) AGE DIFFERENTIATION OF LATE CRETACEOUS-TERTIARY SOURCED OILS

(71) Applicant: ExxonMobil Technology and Engineering Company, Spring, TX (US)

(72) Inventors: Chun Zhu, The Woodlands, TX (US); Weixuan Li, The Woodlands, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 826 days.

(21) Appl. No.: 16/948,054

(22) Filed: Aug. 28, 2020

(65) Prior Publication Data

US 2021/0063378 A1    Mar. 4, 2021

Related U.S. Application Data

(60) Provisional application No. 62/893,533, filed on Aug. 29, 2019.

(51) Int. Cl.
| | | |
|---|---|---|
| *G01N 33/28* | (2006.01) | |
| *G06N 7/00* | (2023.01) | |
| *G06N 7/01* | (2023.01) | |
| *G06Q 10/06* | (2023.01) | |
| *G06Q 10/0631* | (2023.01) | |
| *G06Q 10/0637* | (2023.01) | |

(52) U.S. Cl.
CPC ..... *G01N 33/2823* (2013.01); *G01N 33/2835* (2013.01); *G06N 7/01* (2023.01); *G06Q 10/06315* (2013.01); *G06Q 10/0637* (2013.01)

(58) Field of Classification Search
CPC .. G01N 33/24; G01N 33/241; G01N 33/2823; G01N 33/2835; G06Q 10/0637; G06Q 10/06315; G06Q 50/02; G06N 7/01
USPC .............................. 436/25, 29, 30, 139, 140
See application file for complete search history.

(56) References Cited

U.S. PATENT DOCUMENTS

2016/0153945 A1*  6/2016  Dessort ................. G01N 30/86
                                                          73/23.35

FOREIGN PATENT DOCUMENTS

| WO | 2022/235427 A1 * | 11/2022 |
| WO | 2023/019060 A1 * | 2/2023 |

OTHER PUBLICATIONS

Eiserbeck et al. Journal of Chromatography A, vol. 1218, Jun. 17, 2011, pp. 5549-5553.*
Volk et al. Organic Geochemistry, vol. 36, Dec. 31, 2004, pp. 655-661.*
International Search Report for PCT application No. PCT/US2020/070476 dated Mar. 4, 2021.

(Continued)

*Primary Examiner* — Maureen Wallenhorst
(74) *Attorney, Agent, or Firm* — Lempia Summerfield Katz LLC (57) ABSTRACT

An angiosperm index-1 and an angiosperm index-2 are correlated to an age of a liquid hydrocarbon sample and can be used to distinguish oil age of Late Cretaceous (100-65 million years before present, or 100-65 Ma BP) vs. Paleogene (65-55 Ma BP) vs. Eocene or younger (<55 Ma BP). This method improves over existing methods that cannot distinguish oil age between Late Cretaceous and Miocene (ca. 100-5 Ma BP).

12 Claims, 8 Drawing Sheets

(56) References Cited

OTHER PUBLICATIONS

Burton, Zachary F., et al., "Interpretation of source rock depositional environment and age from seep oil, east coast of New Zealand", International Journal of Earth Sciences, Springer Berlin Heidelberg, Berlin/Heidelberg, vol. 108, No. 4, Jan. 5, 2019, pp. 1079-1091.
Nirmala, D. et al., "Aliphatic hydrocarbon biomarkers of Sekar Kurung Gresik crude oil", Malaysian Journal of Fundamental and Applied Sciences, Jun. 25, 2019, pp. 426-431.
Van Aarssen, B.G.K., "The occurrence of polycyclic sesqui-, tri-, and oligoterpenoids derived from a resinous polymeric cadinene in crude oils from southeast Asia", Geochimica et Cosmochimica Acta., vol. 56, No. 3, Mar. 1992, pp. 1231-1246.
Moldowan et al. (1994) "The Molecular Fossil Record of Oleanane and Its Relation to Angiosperms", Science, vol. 265, Issue 5173, pp. 768-777.

* cited by examiner

AGE DIFFERENTIATION OF LATE CRETACEOUS-TERTIARY SOURCED OILS

CROSS REFERENCE TO RELATED APPLICATION

This application claims the priority benefit of U.S. Provisional Application No. 62/893,533 filed Aug. 29, 2019, the disclosure of which is incorporated herein by reference in its entirety.

BACKGROUND

The present disclosure relates to the dating of (also referred to as the aging of) liquid hydrocarbons (also referred to herein as crude oil). The age of a liquid hydrocarbon, as used herein, refers to the depositional age of the source rock from which the liquid hydrocarbons are derived.

Figure 1:
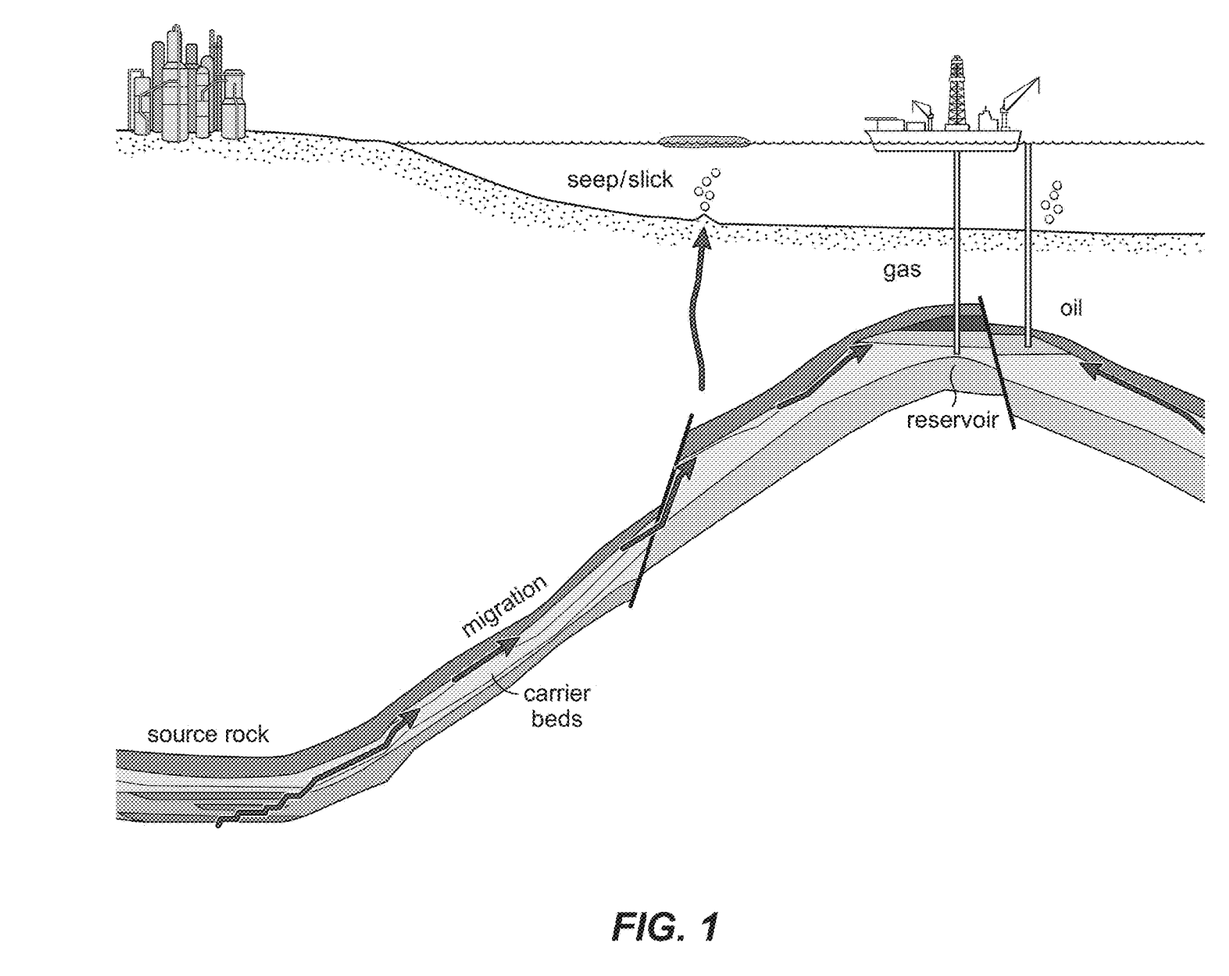
FIG. 1 illustrates the components of a hydrocarbon system in a subsurface region. These components are effective source rock, thermal maturation, reservoir rocks, migration pathway, seal (cap rock), and trap.

Source rocks are organic rich sediments and are the origin of hydrocarbons that have migrated out of source rocks and accumulated in the subsurface. Source rocks are often not penetrable because such rocks are at a great depth. However, sedimentary organic matter preserved in source rocks is transformed into hydrocarbons with increasing temperature and pressure. As illustrated in FIG. 1, the hydrocarbons generated in the source rocks, driven by pressure and buoyancy, migrate through carrier beds and accumulate in sealed geological traps that are more accessible.

Analogous to physical fossils preserved in sediments, oils contain numerous compounds encoding the generative source rock information. More specifically, when an organism fossilizes, the physical fossil remains in the source rock whereas chemicals associated with said physical fossil (or chemical fossils) can leach into the oil. Therefore, just as physical fossils are aged, the chemical fossils can be used to correlate the migrated hydrocarbons to the deeply buried source rocks, from which the oils are derived. These chemical fossils are knowns as biological markers, or biomarkers.

Figure 2:
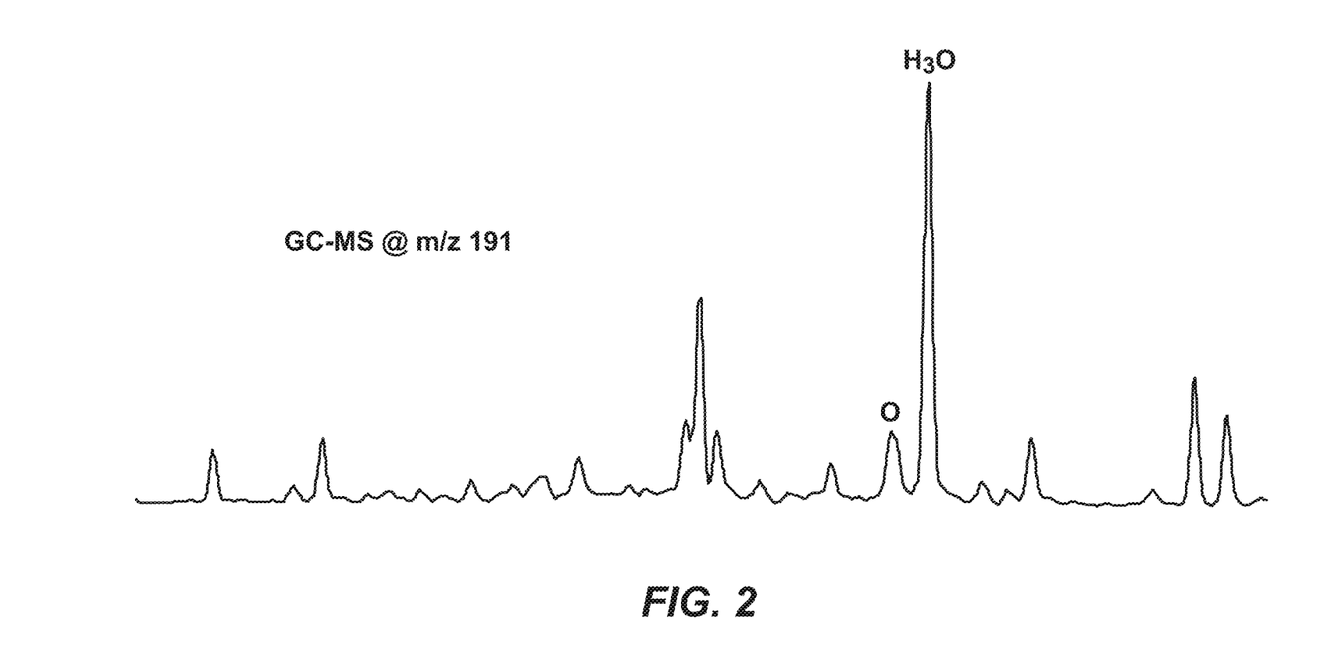
FIG. 2 illustrates an ion chromatograph (m/z 191) of an oil sample where oleanane (O) and $C_{30}$ hopane (H30) are labelled.

For example, angiosperm plants have flowers and produce seeds enclosed within a carpel. As the earth evolved through the Late Cretaceous (100-65 million years before present, or 100-65 Ma BP) epoch through the Paleocene (65-55 Ma BP), Eocene (55-34 Ma BP), Oligocene (34-23 Ma BP), and Miocene (23-5 Ma BP) epochs, angiosperm progressively dominated the higher plant community. Therefore, the presences of angiosperm-specific biomarkers as chemical fossils of angiosperm in oil can be used to constrain the oil age of Late Cretaceous or younger (i.e., <100 Ma BP). More specifically, oleanane (O) is one of the most commonly used angiosperm-specific biomarkers because oleanane survives degradation and is easily analyzed using gas spectroscopy-mass spectroscopy (GC-MS) to identify the presence and quantify the concentration of oleanane. For aging, a relative concentration of oleanane (defined as the concentration ratio of oleanane to hopane (H30)) higher than 0.03 confirms the presence of oleanane and therefore indicates an age of Cretaceous-Tertiary, or <100 Ma BP as described in "The Molecular Fossil Record of Oleanane and Its Relation to Angiosperms," Science 635, 768-777 (1994). FIG. 2 illustrates an ion (m/z 191) chromatograph where oleanane (O) and $C_{30}$ hopane (H30) are labelled. However, an age resolution of <100 Ma BP based on the presence of oleanane is often insufficient to address the hydrocarbon origin in many petroleum basins and makes pinpointing the stratigraphic depth of the corresponding source rocks almost impossible.

SUMMARY OF THE INVENTION

The present disclosure relates to aging oils using angiosperm biomarkers.

A method of the present disclosure includes measuring a concentration of oleanane (O), $C_{29}$ 30-nor-neohopane (H29 Ts), bicadalenes and methyl-bicadalenes (B), and $C_{27}$ 22,29, 30-tris-nor-neohopane (Ts) in a hydrocarbon sample; calculating an angiosperm index-1=[O]/([O]+[H29 Ts]) and an angiosperm index-2=[O]+[B]/([O]+[B]+[Ts]); and estimating an age of the hydrocarbon sample based on a relationship between hydrocarbon age and the angiosperm index-1 and the angiosperm index-2.

The method may further include estimating a probability of the age of the hydrocarbon sample based on a probabilistic analysis of a source data set using a Bayesian inference technique.

The present disclosure also includes a computing device comprising: a processor; a memory coupled to the processor; and instructions provided to the memory, wherein the instructions are executable by the processor to perform a method described herein.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

To facilitate a better understanding of the embodiments of the present invention, the examples of preferred or representative embodiments are given within the detailed description. In no way should the following examples be read to limit, or to define, the scope of the invention.

The present disclosure relates to a new geochemical method for age differentiation of Late Cretaceous-Tertiary sourced oils. The new method allows to the distinguishing of oil age of Late Cretaceous (100-65 Ma BP) vs. Paleogene (65-55 Ma BP) vs. Eocene or younger (<55 Ma BP); and can quantify the likelihood of an age prediction via Bayesian interference technique. This method improves over existing methods that cannot distinguish oil age between Late Cretaceous and Miocene (ca. 100-5 Ma BP).

Figure 3:
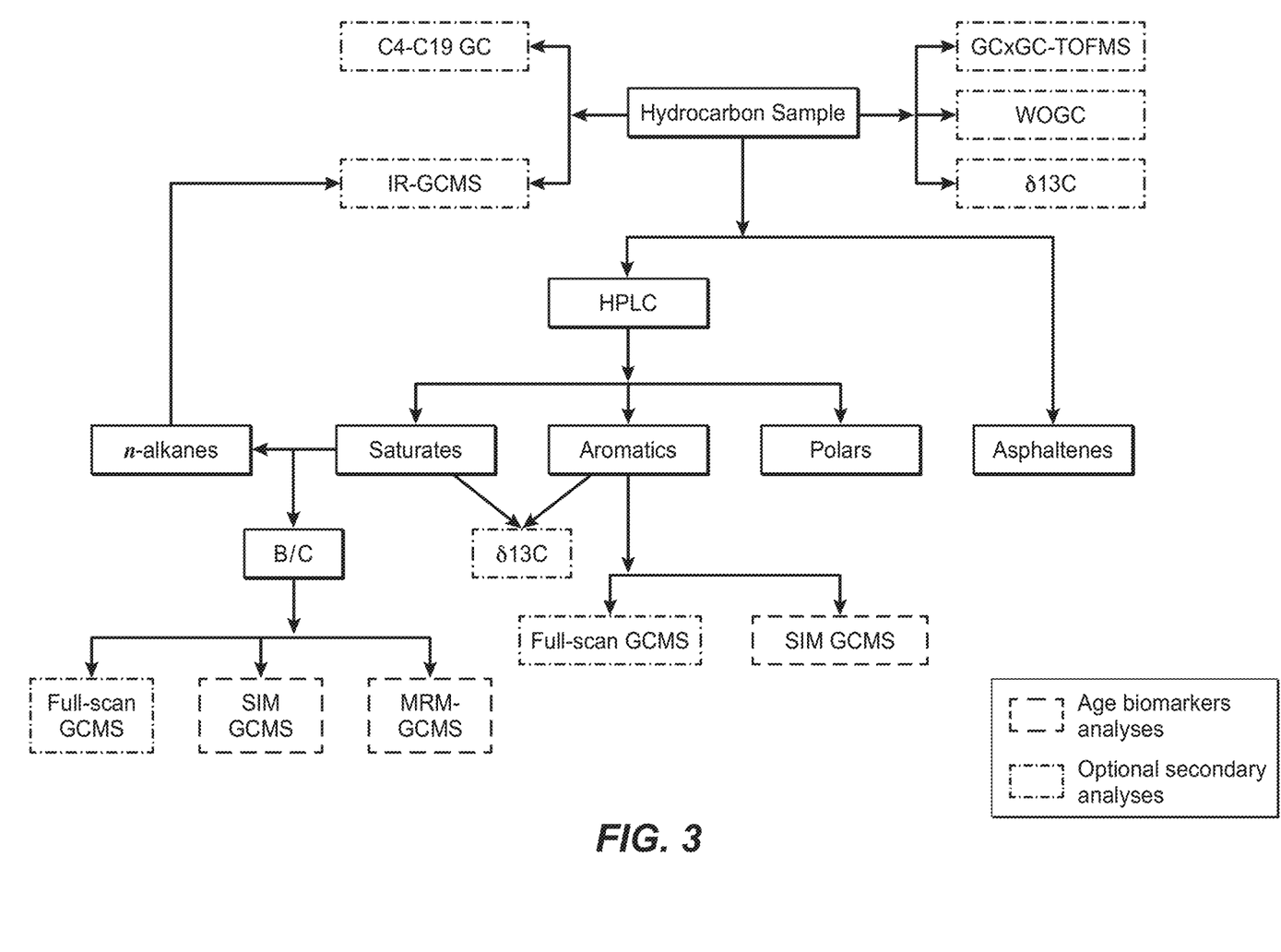
FIG. 3 is a flow diagram of a nonlimiting example analytical workflow of the present disclosure.

Because crude oils are a complex mixture of natural products, the oil samples need to be fractionationed to remove compounds that interfere the detection of age biomarkers. FIG. 3 is a nonlimiting example flow diagram of a sample analytical flowchart for age biomarker analysis. The asphaltenes are extracted from the hydrocarbon sample using n-pentane. The remaining portion of the sample is separated into saturated fraction, aromatic fraction, and polar fraction using high-pressure liquid chromatography (HPLC). The saturated fraction is further purified using a molecular sieve (e.g., ZSM-5) to isolate branched and cyclic alkanes (B/C fraction) by removing the normal alkanes. The B/C fraction is analyzed by selective ion monitoring-gas chromatography/mass spectroscopy (SIM-GC/MS) and metastable reaction monitoring-gas chromatography/mass spectroscopy tandem mass spectroscopy (MRM-GC/MSMS). The aromatics fraction from the HPLC separation is also analyzed by SIM-GCMS.

SIM-GCMS and MRM-GCMSMS techniques have higher resolution than a full-scan GC/MS for more accurate measurements of biomarkers concentrations.

Other secondary analyses may be performed on the whole hydrocarbon sample and fractions thereof to ascertain a level of biodegradation, a level of contamination, sample maturity, sulfur content, American Petroleum Institute (API) gravity, and other characteristics of the hydrocarbon sample. One skilled in the art will recognize suitable analysis techniques for measuring such characteristics. Examples of analysis techniques include, but are not limited to, GCxGC-TOFMS (time of flight mass spectroscopy), whole oil gas chromatography (WOGC), $^{13}C$ isotopic composition ($\delta^{13}C$), full-scan GCMS, infrared (IR)-GCMS, and $C_4$ to $C_{19}$ GC.

GCxGC-TOFMS is used to confirm the chemical structures of age biomarkers preserved in a crude oil sample. WOGC relates to the degrees of biodegradation and artificial contaminations that may impact age biomarker distribution. $\delta^{13}C$ relates to bulk isotopic characteristic of the hydrocarbon sample). $C_4$ to $C_{19}$ GC relates to characteristic of the low molecular weight compounds in the hydrocarbon sample). And, IR-GCMS relates to compound-specific isotope characteristic of the hydrocarbon sample. Any saturates and aromatics fractions are analyzed by $\delta^{13}C$ for the fraction-specific isotopic characteristic of the hydrocarbon sample. The aromatics and the B/C fractions are analyzed by full-scan GCMS to confirm the chemical structures of age biomarkers of the hydrocarbon sample. The n-alkanes separated from the saturates fraction are analyzed by IR-GCMS, which relates to isotopic characteristic of n-alkanes of the hydrocarbon sample).

Any of the foregoing analytical techniques can be replaced or augmented with comparable techniques known to one of skill in the art.

Figure 4:
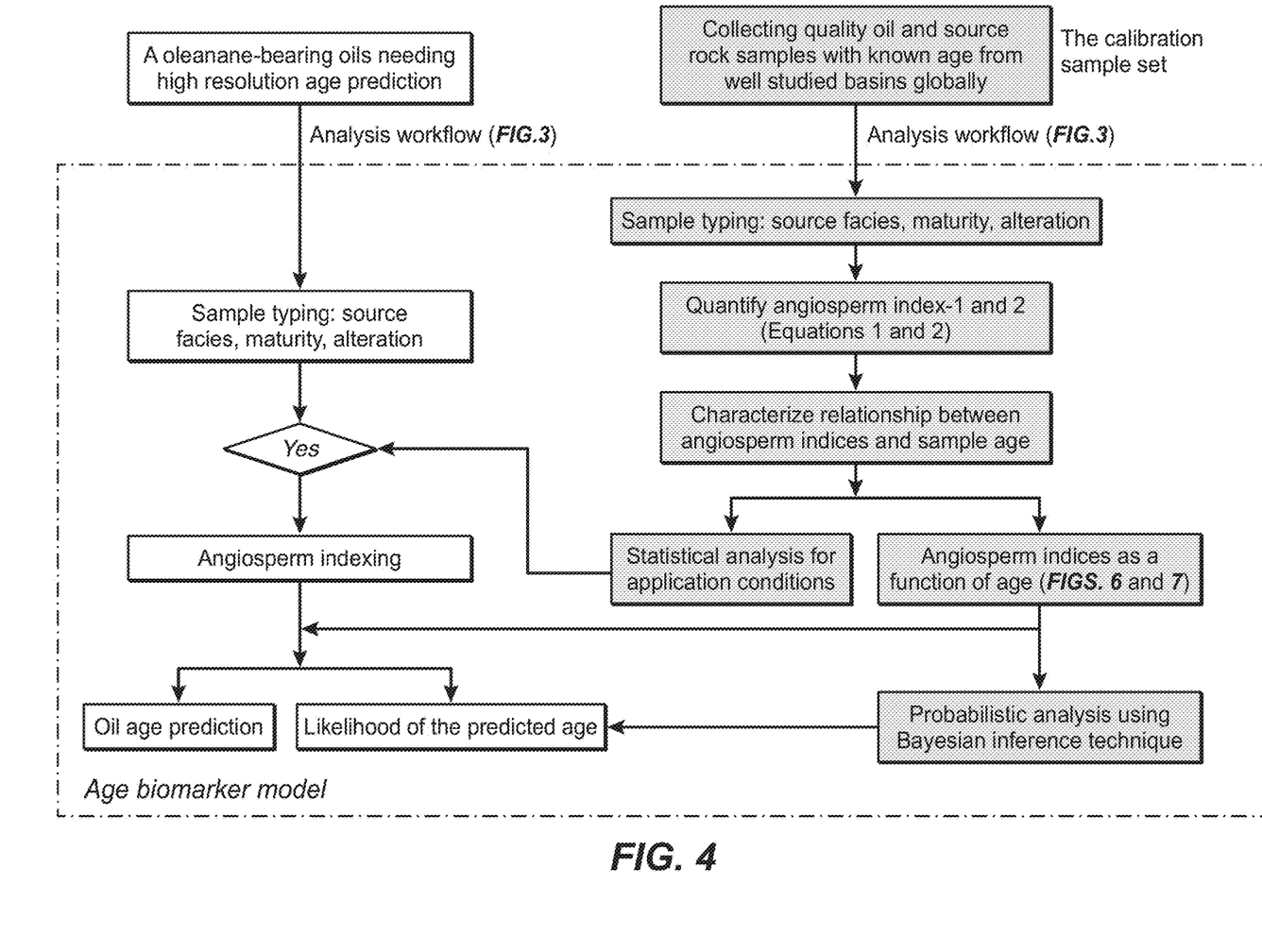
FIG. 4 is a flow diagram of a nonlimiting example age prediction method of the present disclosure.

FIG. 4 is a nonlimiting example flow diagram of a method for age differentiation of Late Cretaceous-Tertiary (<100 Ma BP) soured oils. First, a calibration sample set of quality oil and source rock samples with known specific age during Late Cretaceous-Tertiary period are collected. In the specific example and derivations described relative to FIG. 4, the calibration sample set included over 100 quality oil and source rock samples with known specific age during Late Cretaceous-Tertiary period from well-studied petroleum basins around the world. Accordingly, the new angiosperm indices described herein are applicable to oil samples around the world.

The calibration samples were analyzed by the analytical workflow shown in FIG. 3. From the SIM-GCMS and MRM-GCMS results of the B/C fraction and the SIM-GCMS results of the aromatics fraction, the molecular composition of calibration samples were geochemical characterized in terms of source facies, maturity, and alteration. The other characteristics of the samples derived from secondary analyses may be used (and were used in this example) to confirm the maturity, source facies, and alteration of the oil samples.

Subsequently, the angiosperm biomarkers in these calibration samples were characterized. For low centration samples, the presence of angiosperm biomarkers were confirmed by secondary analysis. The distribution of angiosperm biomarkers were quantified by two novel angiosperm indices:

$$\text{Angiosperm index-1} = [O]/([O]+[H29Ts]) \quad \text{(Equation 1)}$$

$$\text{Angiosperm index-2} = [O]+[B]/([O]+[B]+[Ts]) \quad \text{(Equation 2)}$$

where O is oleanane, H29 Ts is $C_{29}$ 30-nor-neohopane; B is the sum of bicadalenes and methyl-bicadalenes, angiosperm-specific biomarkers; Ts is $C_{27}$ 22,29,30-tris-nor-neohopane.

Oleanane

Bicadinane

Methyl-bicadalene

C$_{27}$ 22,29,30-tris-nor-neohopane

C$_{29}$ 30-nor-neohopane

As used herein, when referring to a relative concentration of a biomarker and when using bracket "[ ]" concentration designations in a formula, the value used may be a true concentration or a value related to concentration. For example, the intensity of a peak in a GCMS chromatogram relates to the concentration of the corresponding composition. Accordingly, the peak intensity can be used as a value related to the concentration in the formulas and methods described herein.

Figure 5:
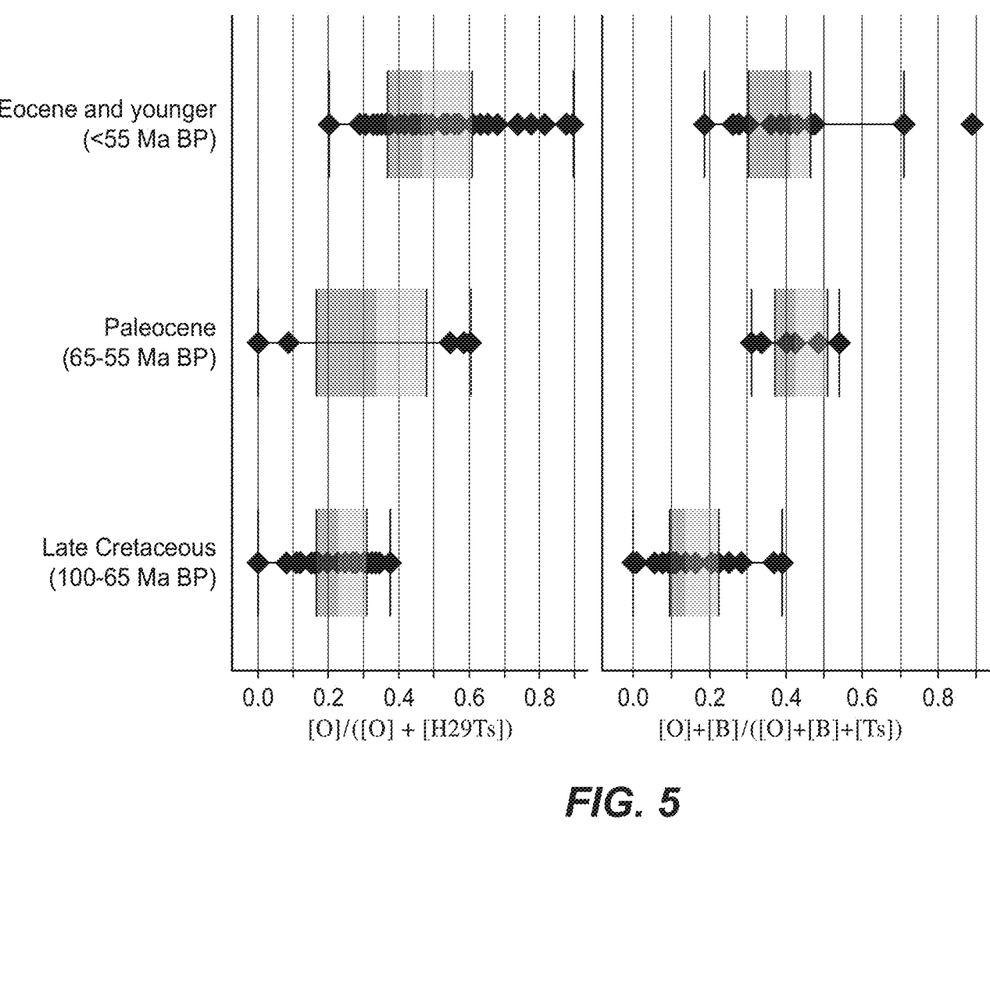
FIG. 5 is a plot of the angiosperm index-1 and angiosperm index-2 values as a function of age of the calibration samples.

Referring again to FIG. 4, the relationship between each of the angiosperm index values and the age of calibration samples was characterized. FIG. 5 illustrates a plot of the epoch of the calibrations samples as a function of each of the angiosperm indices. The observed maximum values for the angiosperm index-1 and angiosperm index-2 for Late Cretaceous were 0.38 and 0.37, respectively. The observed maximum values for the angiosperm index-1 and angiosperm index-2 for Paleocene were 0.6 and 0.53, respectively. Said maxima for the Eocene and younger samples were both close to 1. These values can be used in aging new oil samples.

Figure 6:
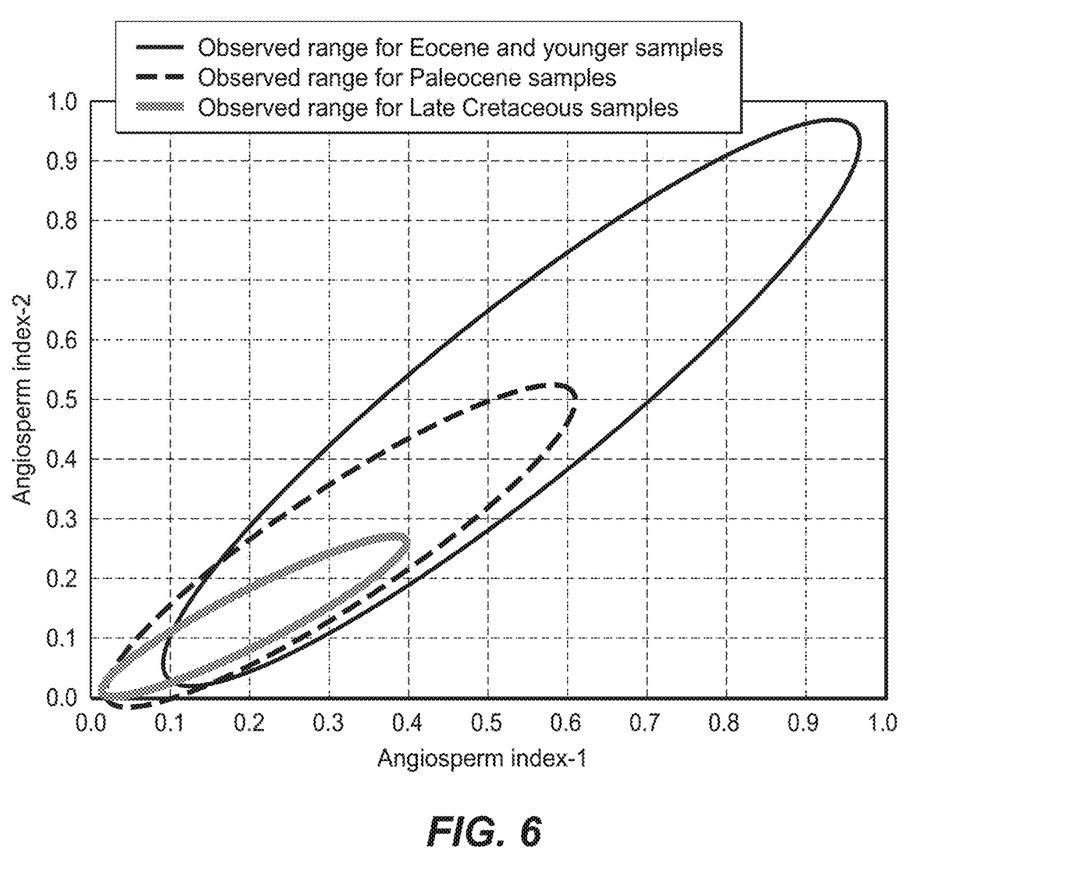
FIG. 6 is a cross-plot of the angiosperm index-1 and angiosperm index-2 with age zones denoted for Late Cretaceous, Paleocene, and Eocene or younger calibration samples.

FIG. 6 is an alternative view of the relationship between each of the angiosperm index values and the age of calibration samples. FIG. 6 is a schematic cross-plot view of the relationship between the angiosperm index-1 and angiosperm index-2 with the epochs outlined within the cross-plot space.

Referring again to FIG. 4, the sample characteristics that should be met for the samples to be properly correlated with angiosperm index-1 and angiosperm index-2 are determined by statistical analysis. In this specific example, a statistical analysis revealed that the two indices primarily correlated with sample age if samples meet the following conditions: 1) maturity level ranges from 8 to 11.5; 2) drilling mud derived contaminations do not interfere the detection of biomarkers used by the angiosperm indices, which can be examined by GC-MS analysis of the mud filtrates; and 3) suitable source facies are deltaic/paralic, lacustrine, terrestrial; whereas oil with marine carbonate source facies may not fit this approach due to lack of terrestrial inputs.

For oleanane-bearing oils, the age can be pre-constrained to Late Cretaceous-Tertiary (100-5 Ma BP) using the published approach (e.g., Moldowen et al., 2014). However, the age resolution of 100-5 Ma BP is often insufficient to allocate the specific origin of oils for most petroleum basins. The new angiosperm indices described herein offer higher resolution age prediction via further differentiation of Late Cretaceous vs. Paleocene vs. Eocene or younger. Per analytical workflow (FIG. 3), the oleanane-bearing oil samples (i.e., Late Cretaceous-Tertiary sourced) that need further age differentiation are prepared and analyzed, the resultant geochemical data are interpreted in terms of source facies, maturity and alteration.

Referring again to FIG. 4, oleanane-bearing oils are analyzed by the workflow in FIG. 3 to determine if the samples satisfy the application conditions of angiosperm indices are proceeded with angiosperm indexing (Equations 1 and 2). If the samples do meet the criteria, the angiosperm index-1 and angiosperm index-2 are determined and compared to the angiosperm indices as a function of age (e.g., FIG. 5 and FIG. 6 or any other mathematical representation (e.g., table, equation, or the like) of said function) to predict an oil age.

Figure 7:
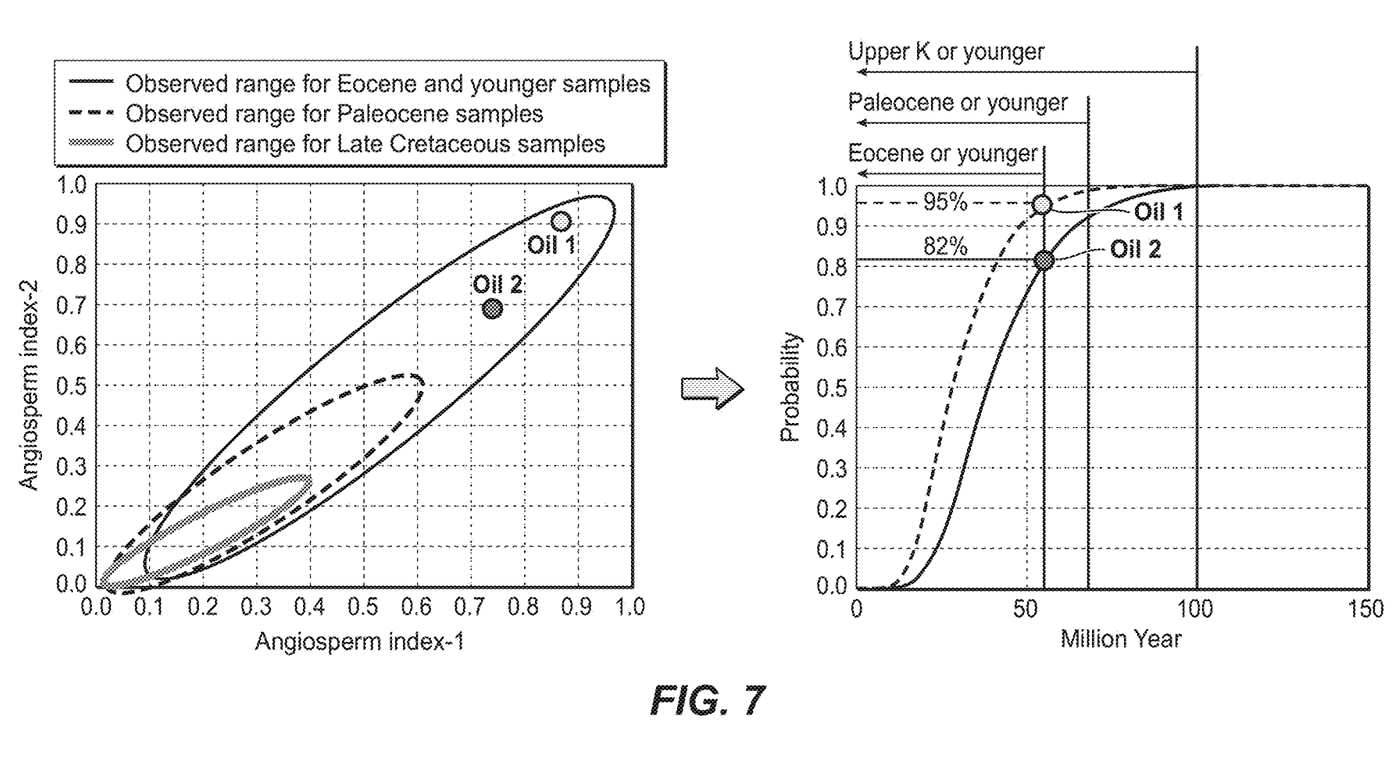
FIG. 7 illustrates the probabilistic analysis of predicted oil age for two hypothetical oil samples.

Finally, a probabilistic analysis may be performed on the data set using Bayesian inference technique (described further below) to derive a conditional probability of age based on the value of the angiosperm indices (FIG. 7). That is, the methods and systems described herein not only provide a greater resolved age but can also provide a likelihood of the accuracy of the age of the hydrocarbon sample, which is a further advantage over current aging techniques.

In Bayesian inference, an unknown quantity of interest is estimated (which, in the methods described herein, is the age of an oil sample and is denoted by $y^*$ hereafter) by combining information from two sources. The first source of information is the observed data, which includes the measured angiosperm indices (Equations 1 and 2) of the oil samples denoted by $x_1^*$ and $x_2^*$. The observed data also include a collection of known indices-age pairs previously measured on n oil samples, $\{(x_1^1, x_2^1, y^1), \ldots, (x_1^n, x_2^n, y^n)\}$.

The second source of information is a confidence level in the relationship between the angiosperm index and the age of the sample. That is, two oil samples with the same index may have different ages. This may be accounted for using the following equation:

$$y = c_0 + c_{11}x_1 + c_{12}(x_1)^2 + c_{21}x_2 + c_{22}(x_2)^2 + \epsilon \quad \text{[Equation 3]}$$

where $\epsilon$ is an error term following a Normal distribution $\epsilon \sim N(0, \sigma^2)$. Note that Equation 3 contains a set of parameters: $\theta = [c_0, c_{11}, c_{12}, c_{21}, c_{22}, \sigma]$. Choosing different parameter values allows for representing a wide range of relationships (e.g., linear/nonlinear dependency, positive/negative correlation, larger/smaller prediction uncertainties, and the like) that are consistent with these assumptions.

Since the exact relation between y and x is unknown, these parameters are treated as random variables following a (prior) probability distribution function (PDF): $p(\theta)$, which reflects the uncertainty we have regarding $\theta$. Also, from Equation 3, the conditional PDF of y given any fixed values of $x_1$, $x_2$, and $\theta$ can be derived. This, again, is a Normal PDF: $p(y|x_1, x_2, \theta) \sim N(\mu, \sigma)$, where $\alpha = c_0 + c_{11}x_1 + c_{12}(x_1)^2 + c_{21}x_2 + c_{22}(x_2)^2$ is the mean.

Next, the information from both sources is combined to achieve an estimate of the oil age of interest $y^*$. First, the joint PDF of $y^*, y^1, \ldots, y^n, \theta$ is derived as follows:

$$p(y^*, y^1, \ldots, y^n, \theta | x_1^*, x_2^*, x_1^1, x_2^1, \ldots, x_1^n, x_2^n) = p(\theta) p(y^*|x_1^*, x_2^*, \theta) \Pi_{i=1}^n p(y^i|x_1^i, x_2^i, \theta) \quad \text{[Equation 4]}$$

Note that the product rule of probability is applied with the assumption that the error terms E for different oil samples are independent. Each factor on the right side of Equation 4 were derived as described further. Then, this PDF is conditioned to the observed values of $y^1, \ldots, y^n$, (i.e., the variables $y^1, \ldots, y^n$ in Equation 4 are fixed to the observed values and rescale Equation 4 such that it is a PDF with respect to the two unknowns $y^*$ and $\theta$).

Equation 5 gives the estimate of unknowns $y^*$ and $\theta$ with all observed data $x_1, x_2^*, x_1^1, x_2^1, \ldots, x_1^n, x_2^n, y^1, \ldots y^n$.

$$p(y^*, \theta | x_1^*, x_2^*, x_1^1, x_2^1, \ldots, x_1^n, x_2^n, y^1, \ldots y^n) \propto p(y^*, y^1, \ldots, y^n, \theta | x_1^*, x_2^*, x_1^1, x_2^1, \ldots, x_1^n, x_2^n)$$ [Equation 5]

In practice, the PDF often lacks a simple analytical form and may be represented with a sample of $y^*$ and $\theta$ generated with a sampling algorithm.

Various aspects of the systems and methods described herein utilize computer systems. Such systems and methods can include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can be performed using computing devices or processor-based devices that include a processor; a memory coupled to the processor; and instructions provided to the memory, wherein the instructions are executable by the processor to perform the methods described herein. The instructions can be a portion of code on a non-transitory computer readable medium. Any suitable processor-based device may be utilized for implementing all or a portion of embodiments of the present techniques, including without limitation personal computers, networks of personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

Applications of Oil Aging

The new method is capable of distinguishing Late Cretaceous vs. Paleocene vs. Eocene or younger sourced oils. It improves age resolution compared with published age biomarker resolution of Late Cretaceous or younger. As such, the new method helps with better understanding of the origin of oils, oil stains, or oil seeps, which allows to de-risk petroleum basins and better differentiates exploration opportunities.

The methods described herein may be used for managing hydrocarbons, and in various hydrocarbon exploration, development, and production activities. As used herein, "hydrocarbon management" or "managing hydrocarbons" includes hydrocarbon exploration, hydrocarbon extraction, hydrocarbon production, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities. As used herein, "hydrocarbon exploration" refers to any activity associated with determining the location of hydrocarbons in subsurface regions. Hydrocarbon exploration normally refers to any activity conducted to obtain measurements through acquisition of measured data associated with the subsurface formation and the associated modeling of the data to identify potential locations of hydrocarbon accumulations. Accordingly, hydrocarbon exploration includes acquiring measurement data, modeling of the measurement data to form subsurface models, and determining the likely locations for hydrocarbon reservoirs within the subsurface. The measurement data may include seismic data, gravity data, magnetic data, electromagnetic data, and the like. As used herein, "hydrocarbon development" refers to any activity associated with planning of extraction and/or access to hydrocarbons in subsurface regions. Hydrocarbon development normally refers to any activity conducted to plan for access to and/or for production of hydrocarbons from the subsurface formation and the associated modeling of the data to identify preferred development approaches and methods. By way of example, hydrocarbon development may include modeling of the subsurface formation and extraction planning for periods of production, determining and planning equipment to be utilized and techniques to be utilized in extracting the hydrocarbons from the subsurface formation, and the like. As used herein, "hydrocarbon production" refers to any activity associated with extracting hydrocarbons from subsurface location, such as a well or other opening. Hydrocarbon production normally refers to any activity conducted to form the wellbore along with any activity in or on the well after the well is completed. Accordingly, hydrocarbon production or extraction includes not only primary hydrocarbon extraction, but also secondary and tertiary production techniques, such as the injection of gas or liquid for increasing drive pressure, mobilizing the hydrocarbon, or treating the well by, for example, chemicals, or hydraulic fracturing the wellbore to promote increased flow, well servicing, well logging, and other well and wellbore treatments.

For example, the specific age of oils or oil stains, or oil seeps ties the samples to a specific stratigraphic interval where hydrocarbons are derived. As a result, hydrocarbon migration pathways from the source to trap can be illustrated. This is critical because the migration pathway determines whether source rocks can effectively charge the reservoir to form economic hydrocarbon accumulation.

In another nonlimiting example, the hydrocarbon generation timing can be calculated based on the specific oil age and the thermal history of the basin. The resultant generation timing is further compared with the timing of trap emplacement. If the trap is deposited after hydrocarbon being generated, the source rock is unlikely to charge the trap and it is considered highly risky to form economic hydrocarbon accumulation.

Other applications of aging and the benefits of better resolved aging per the methods and systems described herein will be apparent to those skilled in the art.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

EXAMPLES

During the Late Cretaceous-Tertiary period (4-100 Ma BP), massive organic rich sediments, particularly those with paralic/deltaic facies, were deposited at different geological ages in the frontier Basin A of the Asia-Pacific region. The presence of numerous oil and gas seeps and pooled hydrocarbons pointed to the presence of active petroleum systems in this region. Oleanane has been detected from many oils of this Basin, indicating Late Cretaceous-Tertiary ages (<100 Ma BP). However, three source rock candidates deposited during Late Cretaceous (100-65 Ma BP), Paleocene (65-55 Ma BP), and Miocene (24-5 Ma), respectively, have been proposed based on regional geology. As such, presence of oleanane is unable to identify the specific source of these migrated hydrocarbons, and consequently migration pathway, charge timing, and source risking remain poorly understood.

Figure 8:
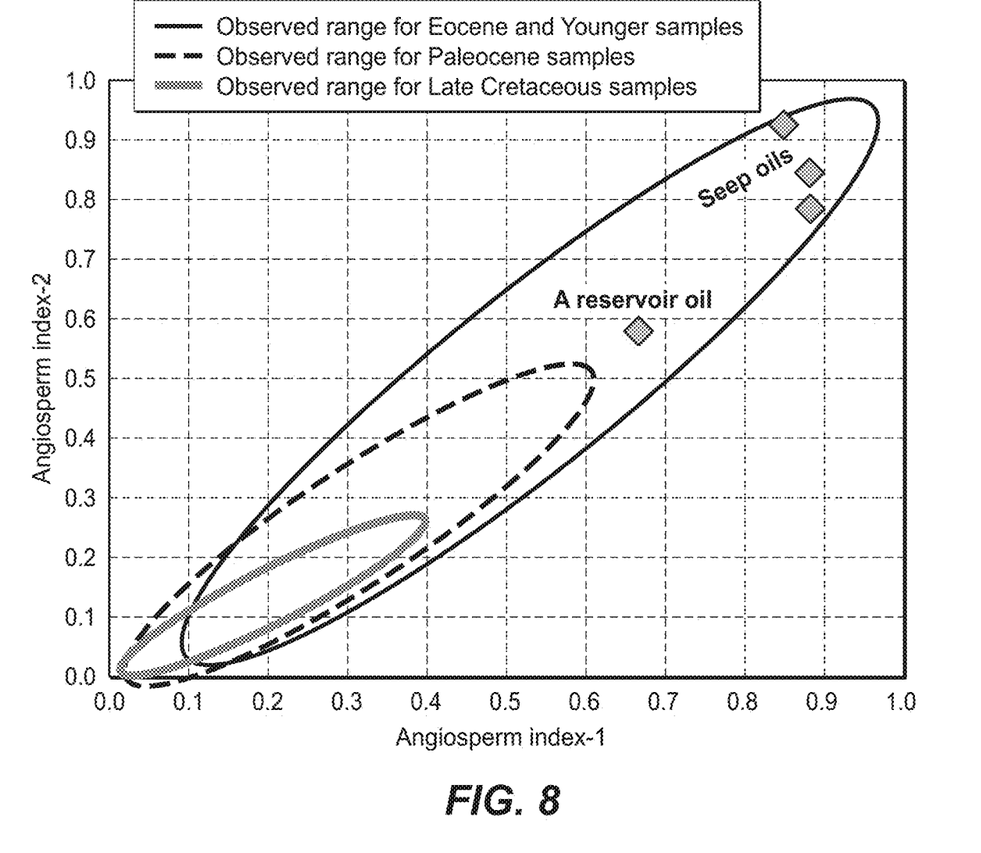
FIG. 8 is a nonlimiting example of the angiosperm index values for seep oils and a reservoir oil from a petroleum basin.

By comparison, our new method constrains the oils using the angiosperm index-1 and 2. The determined indices values of the seep oils and reservoir oil all fall into the Eocene or younger range (<55 Ma BP; FIG. 8). Further probabilistic analysis reveals that the likelihood of the age of the analyzed oils being Eocene or young sourced is >85%. This rules out the Late Cretaceous and Paleocene source rock candidates. It pinpoints Miocene being the most likely source. Upon the specific source rock being detected, the hydrocarbon migration pathway and charge timing can be inferred, which reduces the exploration risk for this basin.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

The invention claimed is:

1. A method comprising:
  measuring a concentration of oleanane (O), $C_{29}$ 30-nor-neohopane (H29Ts), bicadalenes and methyl-bicadalenes (B), and $C_{27}$ 22,29,30-tris-nor-neohopane (Ts) in a hydrocarbon sample obtained from a subsurface location;
  calculating an angiosperm index-1=[O]/([O]+[H29Ts]) and an angiosperm index-2=[O]+[B]/([O]+[B]+[Ts]);
  estimating an age of the hydrocarbon sample based on a relationship between hydrocarbon age and the angiosperm index-1 and the angiosperm index-2;
  using the relationship between the hydrocarbon age and the angiosperm index-1 and the angiosperm index-2 to determine a location from which to extract hydrocarbons from the subsurface location; and
  extracting the hydrocarbons from the determined subsurface location;
  wherein the relationship is determined by measuring the angiosperm index-1 and the angiosperm index-2 of multiple reference hydrocarbon samples having known ages and correlating the measured angiosperm indices-1 and the measured angiosperm indices-2 against the known ages of the multiple reference hydrocarbon samples.

2. The method of claim 1, further comprising:
  estimating a probability of the age of the hydrocarbon sample based on a probabilistic analysis.

3. The method of claim 2, wherein the probabilistic analysis uses a Bayesian inference technique.

4. The method of claim 1, wherein the hydrocarbon sample has a maturity level of 8-11.5.

5. The method of claim 1, further comprising using the estimated age to determine hydrocarbon generation timing.

6. The method of claim 5, wherein the generation timing comprises a timing of trap emplacement.

7. The method of claim 1, further comprising using the estimated age to determine source facies of the hydrocarbon sample.

8. The method of claim 7, wherein the source facies is identified as being deltaic, paralic, lacustrine, or terrestrial.

9. The method of claim 1, wherein using the relationship between the hydrocarbon age and the angiosperm index-1 and the angiosperm index-2 to extract the hydrocarbons comprises:
using the relationship between the hydrocarbon age and the angiosperm index-1 and the angiosperm index-2 to determine hydrocarbon accumulation; and
extracting the hydrocarbons from the determined subsurface location based on the determined hydrocarbon accumulation.

10. The method of claim 9, wherein the hydrocarbon accumulation is determined by:
determining, based on the relationship between the hydrocarbon age and the angiosperm index-1 and the angiosperm index-2, a specific age of oils, oil stains, or oil seeps associated with a specific stratigraphic interval where the hydrocarbon sample is derived;
identifying migration pathways from where the hydrocarbon sample is derived to a geological trap; and
determining, based on the identified migration pathways, the hydrocarbon accumulation.

11. A method comprising:
obtaining a hydrocarbon sample from a hydrocarbon seep in a subsurface location;
measuring a concentration of oleanane (O) C29 30-nor-neohopane (H29Ts), bicadinanes and methyl-bicadinanes (B), and C27 22,29,30-tris-nor-neohopane (Ts) in the hydrocarbon sample;
calculating an angiosperm index-1=[O]/([O]+[H29 Ts]) and an angiosperm index-2=[O]+[B]/([O]+[B]+[Ts]);
estimating an age of the hydrocarbon sample based on a relationship between hydrocarbon age and the angiosperm index-1 and the angiosperm index-2; and
determining, from the estimated age, source rock from which the hydrocarbon sample originated;
using the source rock to determine a location from which to extract hydrocarbons from the subsurface location; and
extracting the hydrocarbons from the determined subsurface location;
wherein the relationship is determined by measuring the angiosperm index-1 and the angiosperm index-2 of multiple reference hydrocarbon samples having known ages and correlating the measured angiosperm indices-1 and the measured angiosperm indices-2 against the known ages of the multiple reference hydrocarbon samples.

12. The method of claim 11, further comprising identifying migration pathways from the source rock to a trap of a hydrocarbon accumulation; and
wherein a specific age of the hydrocarbon sample ties the sample to a specific stratigraphic interval where hydrocarbons of the hydrocarbon sample are derived.

* * * * *